United States Patent [19]

Minagawa et al.

[11] 4,113,678

[45] Sep. 12, 1978

[54] TIN SULFIDE STABILIZER FOR STYRENE POLYMER

[75] Inventors: Motonobu Minagawa, Koshigaya; Toshio Ohzeki, Urawa; Tetsuo Sekiguchi, Hasuda, all of Japan

[73] Assignee: Argus Chemical Corporation, Brooklyn, N.Y.

[21] Appl. No.: 806,521

[22] Filed: Jun. 14, 1977

[30] Foreign Application Priority Data

Jun. 14, 1976 [JP] Japan .................................. 51-69455

[51] Int. Cl.$^2$ .............................................. C08K 5/58
[52] U.S. Cl. ...................... 260/23.7 M; 260/45.75 S; 260/429.7; 260/880 R; 260/880 B
[58] Field of Search ...................... 260/45.75 S, 429.7, 260/2.5 AB, 880 R, 880 B, 23.7 M; 424/288

[56] References Cited

U.S. PATENT DOCUMENTS

| | | | |
|---|---|---|---|
| 3,367,997 | 2/1968 | Smith .............................. | 260/45.75 S |
| 3,413,264 | 11/1968 | Hechenbleikner et al. ... | 260/45.75 S |
| 3,565,930 | 2/1971 | Brecker .............................. | 260/429.7 |
| 3,565,931 | 2/1971 | Brecker .............................. | 260/429.7 |
| 3,890,277 | 6/1975 | Kugele et al. .................. | 260/45.75 S |

FOREIGN PATENT DOCUMENTS

2,306,208  3/1976  France.

*Primary Examiner*—V. P. Hoke
*Attorney, Agent, or Firm*—Otto S. Kauder

[57] ABSTRACT

Processability, color, and mechanical properties upon heating of a rubber modified styrene polymer are improved by incorporating in the polymer a new sulfide compound of four-valent tin having linked to tin through carbon 1 or 2 alkoxycarbonylalkylene groups having 1 to 8 carbon atoms in the alkoxy group and 2 to 3 carbon atoms in the alkylene group.

24 Claims, No Drawings

TIN SULFIDE STABILIZER FOR STYRENE POLYMER

BACKGROUND OF THE INVENTION

This invention relates to rubber modified styrene polymers having as the result of incorporation therein of new tin sulfide compounds improved color, processability, and mechanical properties and retention of these properties upon exposure to elevated temperatures.

Rubber modified styrene polymers are well known. Since the pioneer disclosure of I. Ostromislensky in U.S. Pat. No. 1,613,673 of Jan. 11, 1927, an increasing number of rubber modified styrene polymers has become available in growing quantities. In a 1970 published review of styrene polymers, R. Boyer has quoted estimates that of a total 1969 U.S. production of 1,400,000 tons of styrene polymers (excluding styrenebutadiene synthetic rubber), 57% represent such rubber modified styrene polymers as "high impact" butadiene modified styrene polymer and acrylonitrile-butadiene-styrene (ABS polymers); see N. Bikales (editor), Encyclopedia of Polymer Science and Technology (J. Wiley-Interscience, New York), volume 13, Pages 443 to 446.

The various kinds of rubber modified styrene polymers have in common a two phase or "domain" structure in which hard, glassy portions and softer, elastomeric portions can be distinguished. The rubber modified styrene polymers also share excellent impact properties and can even impart these properties to blends with other hard, glassy polymers, for example the well known impact resistant blends of polyvinyl chloride (PVC) with ABS polymer.

Unmodified ("general purpose" or "crystal") polystyrene is thermally very stable, and is routinely processed at 200°–250° C without objectionable degradation being noticed. The excellent heat stability of unmodified polystyrene is such that molten polymer from each of several polymerization reactors can be fed to a holding tank and from there to extruders as required, thus being kept molten for considerable periods (see Boyer, ibid. pages 131-133) above 200° C.

Rubber modified styrene polymers, on the other hand, are subject to oxidative and thermal degradation at temperatures of 150° C and higher, and stabilization is required to make satisfactory processing possible with minimal changes in melt viscosity, impact strength, and color.

W. Cummings in U.S. Pat. No. 3,267,069 of Aug. 16, 1966 disclosed stabilization against discoloration and degradation of physical properties of ABS polymer by a mixture of zinc sulfide and an ester of 3,3'-thiodipropionic acid such as dilauryl, distearyl, and ditridecyl thiodipropionate. The ABS polymers generally contain 15 to 35 weight % acrylonitrile, 5 to 35% butadiene, and 40 to 80% styrene based on the entire ABS polymer as 100%. The ABS polymer can be a graft copolymer prepared by polymerizing acrylonitrile monomer and styrene monomer in a previously prepared polybutadiene latex or butadiene copolymer rubber latex, or a physical blend of separately prepared acrylonitrile-styrene resin and butadiene-acrylonitrile rubber. C. Bawn, in U.S. Pat. No. 3,352,820 of Nov. 14, 1967 disclosed an ABS plastic composition containing a conventional antioxidant or mixture of antioxidants such as alkylphenyl phosphite and methylenebisalkylphenol, with a Group II metal sulfide added for stabilization against discoloration at elevated temperatures. C. Tholstrup in Canadian Pat. No. 750,469 of Jan. 10, 1967 disclosed the stabilization of an ABS resin, a polyacrylonitrile, a polybutadiene, a polyisoprene, a polychloroprene, and a copoly(butadiene-styrene) resin with a stabilizer mixture consisting essentially of a dialkyl thiodialkanoate and an alkylenebisphenol with the addition of organic phosphite optional. Sanyo Chemical in Japanese Patent publication 14324/68 of June 17, 1968 disclosed improving thermal resistance of ABS resin with a lithium, sodium, potassium, calcium, or magnesium salt of a phosphoric acid ester of an organic hydroxy compound having a hydrocarbon group of at least 6 carbon atoms. K. Ott in U.S. Pat. No. 3,414,636 of Dec. 3, 1968 disclosed copolymer mixtures of a butadiene elastomer and a thermoplastic copolymer of styrene and acrylonitrile having excellent thermal stability as a result of admixing a small amount of composition consisting of 2,2'-methylenebis-4-methyl-6-cyclohexylphenol and zinc sulfide. Ott's copolymer mixtures are defined as 5 to 60% by weight of rubber-elastic copolymer of butadiene and 95 to 40% by weight of thermoplastic component consisting of 50 to 95% styrene and 50 to 5% acrylonitrile. A. Hecker in U.S. Pat. No. 3,472,813 of Oct. 14, 1969 disclosed a stabilizer composition for ABS polymers consisting essentially of an alkyl pyrophosphate salt of a monovalent or bivalent metal cation or an ammonium, quaternary ammonium, or amine cation, and a polyhydric polycyclic phenol, and in U.S. Pat. No. 3,520,952 of July 21, 1970 the same stabilizer composition for block copolymers containing a non-elastomeric block which is a polymer of an alpha-olefin, and an elastomeric block which is a polymer of a conjugated diolefin. P. Marinacci in U.S. Pat. No. 3,637,555 of Jan. 25, 1972 disclosed a multi-component combination of antioxidants for stabilizing ABS type copolymers subject to oxidative and heat degradation, containing a diester of thiodipropionic acid, 2,6-di-t-butyl-4-methylphenol, a 2,2'-methylenebis(4-alkyl-6-t-alkylphenol), and an epoxide compound, with the optional use in addition of an alkylated aromatic phosphite and calcium stearate. C. Abramoff in U.S. Pat. No. 3,856,728 of Dec. 24, 1974 disclosed a stabilizer system for ABS polymers, both pigmented and unpigmented, comprising an organic phosphite, a polyhydric polycyclic phenol, and an epoxy compound. T. Ohzeki in Japan Kokai No. 4244/76 of Jan. 14, 1976 disclosed ABS resin and high-impact butadiene-modified polystyrene comprising an organic phosphite and a pinene-substituted bisphenol. A. Kennedy in U.S. Pat. No. 3,907,932 of Sept. 23, 1975 disclosed the stabilization of olefinic nitrile polymers including copolymers with styrene and butadiene containing at least 50% of the olefinic nitrile with dialkyltin maleate compounds having the formula $(R_2SnC_4H_2O_4)_x$ or $R_2Sn(C_4H_2O_4R')_2$ in which R is alkyl with 2 to 12 carbons, R' is alkyl with 4 to 14 carbons and $x$ is an integer from 1 to 4.

Kennedy points out that a number of other alkyltin compounds known as stabilizers for polyvinyl chloride (PVC) are unsatisfactory in her polymers. Earlier disclosures of tin compounds in rubber modified styrene polymers include ABS polymer with 0.02–10% of $(R_1R_2R_3Sn)_aX$ where $R_1$ and $R_2$ are hydrocarbon, $R_3$ is hydrocarbon or X, X, is thiol acid, aliphatic or aromatic mercaptan, or an ester thereof, by Nitto Kasei Co. in Japanese publication No. 16187/66 of Sept. 12, 1966; also dialkyltin aliphatic carboxylates together with phosphite diesters and triesters by M. Watanabe in Japan publication 22531/67 of Nov. 4, 1967.

There is an enormous number of disclosures of tin compounds used to stabilize PVC compositions, some of which contain minor amounts of ABS polymers to improve impact resistance. To illustrate the unmanageably large bulk of this literature, it might be noted that a 1959 review booklet by H. Verity Smith titled "The Development of the Organotin Stabilizer" (published by Tin Research Institute, Greenford, England) listed over 100 patent disclosures of tin containing stabilizers for PVC, and more recently C. Stapfer in U.S. Pat. No. 3,830,751 of Aug. 20, 1974 listed over 500 individual tin containing compounds and L. Weisfeld in U.S. Pat. No. 3,887,519 of June 3, 1975 listed over 200 compounds that are all methyltin derivatives, i.e. compounds with at least one methyl group directly linked to tin, including for example dimethyltin sulfide. Overwhelmingly the tin containing stabilizers referred to in this literature are tin compounds having at least one hydrocarbon group linked to 4-valent tin through carbon, for example methyl, n-butyl, and n-octyl. The remarkably small number of disclosures of tin containing stabilizers other than 4-valent tin derivatives with at least one hydrocarbon group linked to tin are represented by J. Fincke U.S. Pat. No. 2,479,918 of Aug. 23, 1949, tetra(2-thienyltin); S. Caldwell U.S. Pat. No. 2,629,700 of Feb. 24, 1953, carboxylate salts of 2-valent (stannous) tin; W. Leistner U.S. Pat. No. 2,726,227 of Dec. 6, 1955, certain tetrahydrocarbon mercaptides of tin having only hydrocarbon groups linked to tin through sulfur; W. Considine in U.S. Pat. No. 3,412,120 of Nov. 19, 1968 disclosed cyanoalkylenetin sulfides having linked to tin one or two cyanoalkylene groups having two or more carbon atoms in the alkylene group made from tetrakis (cyanoalkylene)tin by halogenation or redistribution to the required cyanoalkylenetin halide; Considine also showed in U.S. Pat. No. 3,454,609 of July 8, 1969 that when cyanoalkylenetin compounds were hydrolyzed, polymeric propionatotin compounds were obtained. Akzo N.V. in Netherlands Specification 74-12230 of Mar. 16, 1976 disclosed functional substituted organotin trihalides prepared from stannous halide, hydrogen halide, and carbonyl group activated olefins of the type $R_1R_2'C=CR_3R_4$ where at least one R group is an activating group with a carbonyl radical adjoining the double bond and the other R groups are hydrogen or alkyl groups, and converted to mercaptoester type stabilizers; Akzo N.V. Netherlands Specification No. 75-03116 of Sept. 17, 1976 disclosed functional substituted organotin dihalides prepared from tin metal, hydrogen halide, and carbonyl group activated olefins of the type $R_1R_2C=CR_3R_4$ where at least one R group is an oxygen containing group with a carbonyl group adjoining the double bond and the other R groups are hydrogen or alkyl groups, and converted to stabilizers by reaction with alkylthiocarboxylic acid esters, alkylthiols, monocarboxylic acids, or partial esters of dicarboxylic acids.

Pertinent to the evaluation of the present invention among the large number of known hydrocarbontin sulfur compounds are particularly the use of hydrocarbontin sulfides by E. Weinberg in U.S. Pat. Nos. 2,746,946 of May 22, 1956 and 2,789,103 of Apr. 16, 1957; and by M. Crauland in U.S. Pat. No. 3,108,126 of Oct. 22, 1963; alkylstannonic acids and alkylthiostannonic acids (i.e. monohydrocarbontin sulfides) by H. Frey in U.S. Pat. No. 3,021,302 of Feb. 13, 1962; cyclic dihydrocarbyltin salts of mercapto carboxylic acids by G. Mack in U.S. Pat. No. 3,027,350 of Mar. 27, 1962; thiobis (dihydrocarbontin) salts of carboxylic acids and dicarboxylic acid monoesters by A. Schroeder in U.S. Pat. No. 3,476,404 of Nov. 4, 1969; an organotin stabilizing agent obtained by reacting a compound of the formula $R—Sn—(X)_3$ wherein R is a hydrocarbon and X halogen, with a mixture of an alkali metal sufide and (a) aliphatic alkali metal mercaptide or (b) an alkali metal salt of a saturated or unsaturated mono or polycarboxylic acid, by C. Dorfelt in U.S. Pat. No. 3,442,852 of May 6, 1969; organotin mercaptoacid ester sulfides having the formula:

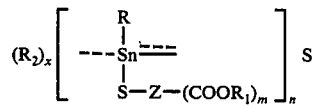

in which n is an integer from one to two, m is the number of $COOR_1$ groups, and is an integer from one to four, x is an integer from zero to one, R is a hydrocarbon radical having from about one to about eighteen carbon atoms, and preferably from four to eight carbon atoms, $R_1$ is an organic group derived from a monohydric or polyhydric alcohol of the formula $R(OH)_{n_4}$, where $n_4$ is an integer from one to about four, but is preferably one or two; $R_2$ is R or $SZ(COOR_1)_m$; Z is a bivalent alkylene radical carrying the S group in a position alpha or beta to a $COOR_1$ group, and can contain additional free carboxylic acid, carboxylic ester, or carboxylic acid salt groups, and mercapto groups; and the Z radical has from one to about five carbon atoms, by O. Kauder in U.S. Pat. No. 3,565,930 of Feb. 23, 1971; reaction products of organotin mercaptoacid derivatives having the formula

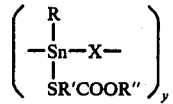

as well as $R_nS_n(SR'COOR'')_{4-n}$ and $(RSn(SR'COOR'')_2)_2X$ wherein R is an alkyl radical having up to 12 carbons, R" is an alkyl radical, R' is an alkylene group of at least 2 methylene groups, X is oxygen or sulfur, n is 1 to 3 and y designates the degree of polymerization, with an organotin oxide, a monohydrocarbyltin oxide, or a hydrocarbylstannoic acid or ester thereof, by L. Weisfeld in U.S. Pat. No. 3,576,785 of Apr. 27, 1971; and alkyltin polysulfide thioesters having the formula $(R_xSn)_n(—SR'COOR'')_{(4-x)n-2m}(—S_y)_m$ where the tin is tetravalent, R is alkyl of 1 to 8 carbon atoms or benzyl, R' is alkylene of 1 to 4 carbon atoms, R" is alkyl of 1 to 18 carbon atoms or alkenyl of 2 to 18 carbon atoms, cycloalkyl having 5 to 6 carbon atoms in the ring, or benzyl, x is 1 or 2, y is 2 to 4, n is 1 to 10 and m is $\frac{1}{2}n$ to n, by T. Kugele in U.S. Pat. No. 3,869,487 of Mar. 4, 1975.

SUMMARY OF THE INVENTION

According to this invention, the processability, color, and mechanical properties upon heating of a rubber modified styrene polymer composition are improved by incorporating in the polymer composition a new sulfide compound of four-valent tin having linked to tin through carbon from 1 to 2 alkoxycarbonylalkylene groups having 1 to 8 carbon atoms in the alkoxy group and 2 to 3 carbon atoms in the alkylene group, and directly linked to tin at least one bivalent sulfide group. Amides and Group II metal salts of carboxylic acids having 8 to 26 carbon atoms can be included with the new sulfide compound to provide a composition whose ingredients interact cooperatively to provide further improvement in the rubber modified styrene polymer.

Small amounts of the new sulfide compound are effective, ranging from 0.005 to 5% by weight of the rubber modified styrene polymer. When the new sulfide compound is used together with an amide or Group II metal salt of a carboxylic acid, the proportions of the latter relative to the new sulfide range from 5 to 1 to 1 to 5 by weight.

DESCRIPTION OF PREFERRED EMBODIMENTS

In the new sulfide compound of tin according to this invention, the term "sulfide" refers to the sulfide group $-S_a(C_bH_{2b}CO_2)_c-$, wherein $a$ is 1 to 4, $b$ is 1 to 2, $c$ is 0 or 1 and the terminal valences are linked to the same tin atom or to different tin atoms. Each such tin sulfide compound contains per tin atom one or two alkoxycarbonylalkylene groups linked to tin through carbon and from one to four sulfide groups.

Thus the term "sulfide" includes monosulfides, disulfides, trisulfides, tetrasulfides, and carboxyalkylene sulfides.

The alkoxycarbonylalkylene group linked to tin through carbon has from one to about eight carbon atoms in the alkoxy group and from two to three carbon atoms in the alkylene group. Lower homologs with a single carbon atom in this alkylene group are unsatisfactory.

In addition, the new sulfide compound of tin according to this invention can contain per tin atom one or two alkoxycarbonylalkylene mercapto groups linked to tin through sulfur. An alkoxycarbonylalkylene mercapto group linked to tin through sulfur has from four to about eighteen carbon atoms in the alkoxy group and from one to two carbon atoms in the alkylene group.

Sulfide compounds of tin having linked to tin only suflide groups, and alkoxycarbonylalkylene groups linked to tin through carbon, can be defined by the formula;

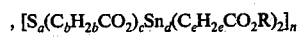
, $[S_a(C_bH_{2b}CO_2)_cSn_d(C_eH_{2e}CO_2R)_2]_n$ in which R is an alkyl group having from one to eight carbon atoms, $a$ is an integer from 1 to 4, $b$ is 1 or 2, $c$ is 0 or 1, $d$ is 1 or 2, $e$ is 2 or 3, and $n$ is from 1 to about 100, provided that when $d$ is 2 $a$ is at least 3.

The R groups are alkyl groups having from one to eight carbon atoms, for example methyl, ethyl, propyl, isopropyl, isobutyl, s-butyl, n-butyl, t-butyl, isohexyl, n-octyl, isooctyl, 2-ethylhexyl, and 2-octyl, n-amyl, and 2-methylbutyl.

When d in the above formula is one, the compound is a bis(alkoxycarbonylalkylene) tin sulfide, and R $a$, $b$, $c$, $e$, and $n$ are as defined above. Thus the atomic ratio of sulphur to tin is from 1 to 1 to 4 to 1.

When in such a compound $c$ is one, the compound is a bis(alkoxycarbonylalkylene) tin carboxyalkyl sulfide, for example bis(methoxycarbonylethylene) tin 2-carboxyethyl sulfide, bis(ethoxycarboxylethylene)tin carboxymethyl sulfide, and S,O-bis(thiomethoxycarbonylethylenetin)3-mercaptopropionate. The sulfide and carboxyl groups can be linked to the same tin atom or to different tin atoms.

When $c$ is zero, a type of the compound has the recurring group

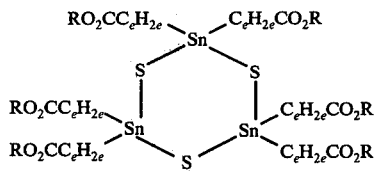

where $n$ is the number of units in the chain, and ranges up to 100 and more.

Another way of defining the type $SSn(C_eH_{2e}CO_2R)_2$, i.e. a bis(alkoxycarbonylalkylene) tin sulfide of the above formula in which $a$ is one and $c$ is zero is

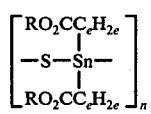

Exemplary of this type are: bis(2-methoxycarbonylethylene)tin sulfide trimer, bis(2-methoxycarbonylethylene)tin sulfide polymer, bis(2-methoxycarbonylpropylene)tin sulfide polymer, bis(2-propoxycarbonylethylene)tin sulfide polymer, and bis(2-ethoxycarbonylethylene)tin sulfide polymer.

The two alkoxycarbonylalkylene groups linked to tin in this type can be the same or different. Compounds where two different alkoxycarbonylalkylene groups are linked to tin through carbon include 2-methoxycarbonylethylene-2-methoxycarbonyl-2-methylethylene tin sulfide and 2-propoxycarbonylethylene-2-ethoxycarbonylethylene tin sulfide.

When in the above formula $d$ is two, there is one alkoxycarbonylalkylene group linked to tin through carbon for each tin atom.

These mono(alkoxycarbonylalkylene) tin sulfides of this invention are polymers which can be illustrated by the formulae

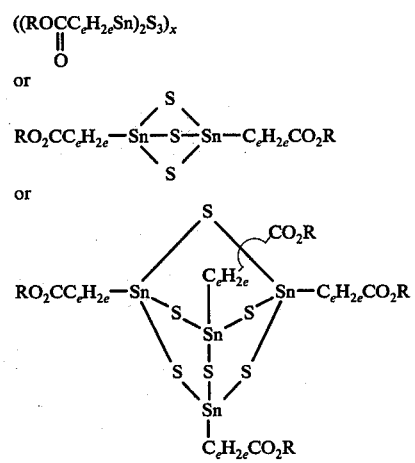

in which each tin atom is linked to three sulfur atoms and each sulfur is linked to two tin atoms, and x is a number from one to about 100.

Exemplary mono(alkoxycarbonylalkylene)tin sulfides of this type include 2-methoxycarbonylethylene tin sulfide polymer, 2-ethoxycarbonylpropylene tin sulfide polymer, 2-butoxycarbonylethylene tin sulfide polymer, and 2-isopropoxycarbonylenethyl tin sulfide polymer.

When the tin sulfide compound of this invention has one or two mercaptoalkylenecarboxylic acid ester groups linked to tin through sulfur in addition to sulfide groups, and alkoxycarbonylalkylene groups linked to tin through carbon, the compound can have the formula:

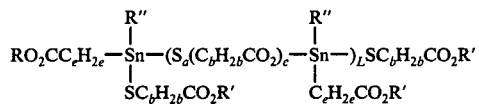

in which R' is a hydrocarbon group having from four to about 18 carbon atoms, R" can be $-C_eH_{2e}CO_2R$ and $-SC_bH_{2b}CO_2R'$, L is a number from one to ten, and R, a, b, c and e are as defined above. The R' hydrocarbon groups in the above formula can be selected from among alkyl, cycloalkyl, alkylcycloalkyl, cycloalkylalkyl, and arylalkyl having from four to about eighteen carbon atoms. Alkyl groups of 4 to 18 carbon atoms are preferred. Typical R' groups are n-butyl, isobutyl, 4-methyl-2-pentyl, n-hexyl, 2-ethylhexyl, n-octyl, isooctyl, 3,5,5-trimethylhexyl, isodecyl, lauryl, tridecyl, $C_{12}$ to $C_{15}$ linear alkyl, cetyl, n-octadecyl, cyclopentyl, 3,5,5-trimethylcyclohexyl, tricyclodecyl, and dimethylbenzyl.

The alkoxycarbonylalkylene tin sulfide mercaptoalkylenecarboxylic acid esters include sulfides with sulfide groups linking tin atoms each carrying two alkoxycarbonylalkylene groups linked through carbon such as bis(bis(2-methoxycarbonylethylene)tin isooctylthioglycolate)sulfide, bis(bis(2-methoxycarbonylethylene)tin isooctylthioglycolate)disulfide, bis(bis(2-methoxycarbonylethylene)tin isooctylthioglycolate) tetrasulfide, and S, O-bis(2-methoxycarbonylethylene)tin isooctyl 3-mercaptopropionate) mercaptopropionate; sulfides with sulfur linking tin atoms each carrying one alkoxycarbonylalkylene group linked through carbon such as bis(2-methoxycarbonylene tin bis(2-ethylhexylthioglycolate)) trisulfide, and bis(2-methoxycarbonylethylene tin bis(2-ethylhexylthioglycolate)) tetrasulfide, and sulfides with sulfur linking tin atoms carrying one alkoxycarbonylalkylene group linked through carbon and tin atoms carrying two alkoxycarbonylalkylene groups linked through carbon, such as 2-methoxycarbonylethylene tin bis(isooctylthioglycolate)-bis(2-methoxycarbonylethylene)tin isooctyl thioglycolate sulfide, and the related disulfide, trisulfide, and tetrasulfide, as well as 2-methoxycarbonylethylenetin bis(isooctylthioglycolate)-bis(2-methoxycarbonylethylene)tin isooctylthioglycolate-S,O-3-mercaptopropionate.

The new tin sulfides of this invention can be prepared by a number of procedures. For example, hydrogen sulfide can be bubbled at about 40° C into a slurry of alkoxycarbonylalkylene tin oxide in water or an organic solvent (such as methanol, acetone, or toluene). The insoluble oxide is converted to a solution or dispersion of the sulfide and the reaction is terminated when the entire system is liquefied.

The required alkoxycarbonylalkylene tin oxide can be obtained from an alkoxycarbonylalkylene tin halide by treatment with alkali bicarbonate as disclosed by S. Matsuda et al in Chemical Abstracts 1966, Vol. 65, 18613b. The halide can be made by the reaction of tin metal with an alkoxycarbonylalkylenating agent, for example an alkoxycarbonylalkylene halide (see S. Matsuda U.S. Pat. No.3,440,255 of Apr. 22, 1969), or a hydrogen halide with an alkoxycarbonylalkene (see Netherlands Specification 75/03116 of Sept. 18, 1976).

Avoiding the preparation and isolation of alkoxycarbonylalkylene tin oxide, during which a wasteful side reaction can remove the alkoxy group and precipitate a very insoluble carboxyalkylene tin salt, provides an even more useful technique i.e. the displacement of alkoxycarbonylalkylene tin halides (e.g. (MeO-COCH$_2$CH$_2$)$_2$SnCl$_2$ by an aqueous alkali metal sulfide or ammonium sulfide. (In this and following formulas Me represents a methyl group).

The above preparative methods can be summarized in the transformations below, where the methoxycarbonylethylene tin compounds shown are representative of the entire class of alkoxycarbonylalkylene tin compounds:

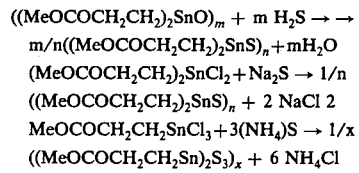

Carboxyalkylene sulfides are prepared by analogous transformations using a carboxyalkylene sulfide salt or acid starting material.

These preparations are carried out in an aqueous or aqueous-alcoholic medium, from which the desired product separates as a solid or a separate liquid phase. A water-immiscible organic solvent can be used to take up the product as it forms and assist separation from the inorganic salt solution by-product; suitable solvents include hexane, heptane, toluene, xylene, chloroform, ethylene dichloride, ethyl acetate and butyl acetate.

The alkoxycarbonylalkylene tin sulfide mercapto alkylenecarboxylic acid ester sulfides of the invention can be prepared by reacting bis(alkoxycarbonylalkylene halides, mono-alkoxycarbonylalkylene tin halides or mixtures thereof, at a temperature within the range from about 25° to about 200° C with less than stoichiometric amounts of mercapto alkylenecarboxylic acid ester, and the resulting alkoxycarbonylalkylene mercapto alkylenecarboxylic acid ester halide intermediate can be further reacted with alkali or alkaline earth metal sulfides, such as sodium sulfide or ammonium polysulfide, to produce alkoxycarbonylalkylene tin mercapto alkylenecarboxylic acid ester sulfide. The following schemes show the reactions that are involved, in the case of mono(alkoxycarbonylalkylene) tin compounds (I) and bis(alkoxycarbonylalkylene) tin compounds (II), where X indicates a halogen atom such as bromide or chloride, n is from one to two, and R, R',L,a,b,and e are as defined above.

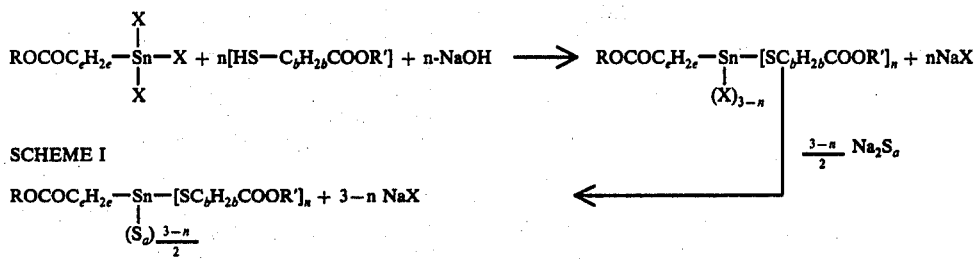

SCHEME I $ROCOC_eH_{2e}$—Sn—[$SC_bH_{2b}COOR'$]$_n$ + $\frac{3-n}{2}$ NaX
   |
   ($S_a$)$_{\frac{3-n}{2}}$ When n is one the molecular structure corresponds to monomeric formula A-1, cyclic formula A-2 or polymeric formula A-3; when n is two the molecular structure corresponds to formula B.

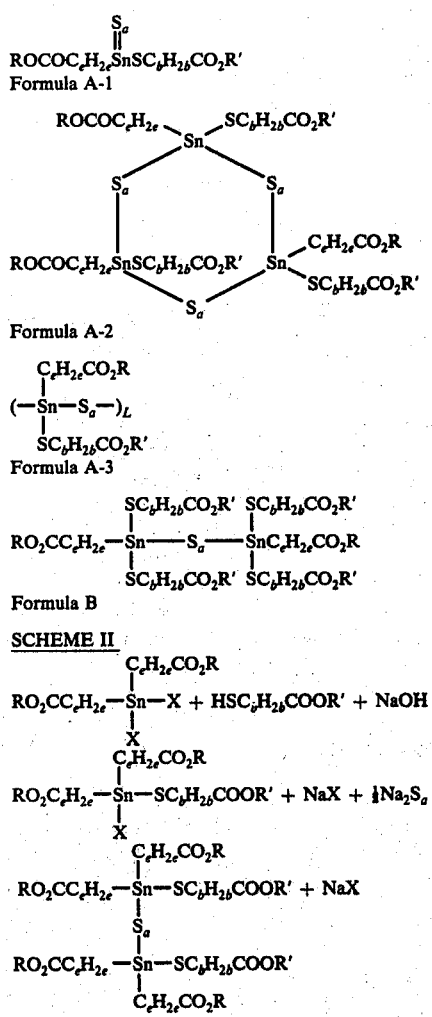

Formula A-1

Formula A-2

Formula A-3

Formula B

SCHEME II

Thus Scheme I illustrates the preparation of monoalkoxycarbonylalkylene tin mercaptoalkylenecarboxylic acid ester sulfides, and Scheme II the reaction for the preparation of bis(alkoxycarbonylalkylene) tin mercapto alkylenecarboxylic acid ester sulfides.

In the steps of reacting the alkoxycarbonylalkylene tin halide with the mercpatoalkylenecarboxylic acid acid ester and alkali, and of reacting the alkoxycarbonylalkylene tin mercapto alkylenecarboxylic acid ester halide with alkali metal or alkaline earth metal sulfide, it is important to take care that the pH of the reaction mixture does not exceed about 10, i.e., become strongly basic, by too rapid addition of alkali hydroxide or sulfide, or addition of excess alkali hydroxide and sulfide, since this may result in undesired hydrolysis of the mercaptoalkylenecarboxylic acid ester group and/or the alkoxycarbonylalkylene tin group. Where the alkoxycarbonylalkylenetin mercaptoalkylenecarboxylic acid ester sulfide is being prepared, it will be understood that the production can have the formulas shown by A or B, above, or both can exist in admixture, according to the relative proportion of mercaptoalkylenecarboxylic acid ester and of sulfide reaction with the alkoxycarbonylalkylenetin halide. Compound B has one-half the equivalents of sulfide sulfur of compound A.

Similarly, mixed monoalkoxycarbonylalkylenetin bis(alkoxycarbonylalkylene) tin compounds of the type of formulas C and D are obtained by using a mixture of monoalkoxycarbonylalkylene tin trihalide and bis(alkoxycarbonylalkylene) tin halide starting materials, as shown in scheme III SCHEME III
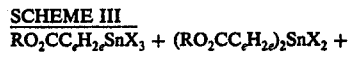

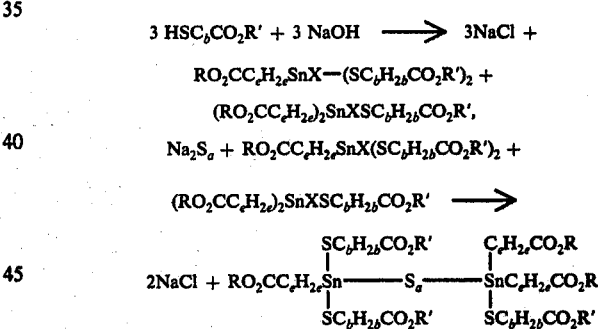

When other than stoichiometric proportion of alkoxycarbonylalkylenetin halide mercaptoalkylenecarboxylic acid ester and/or alkali sulfide are reacted, polymers are obtained. For example, as the ratio of mercaptoalkylenecarboxylic acid ester to alkali sulfide is increased from n=1 to n=2 in scheme I, compounds of the type of formula D are obtained.

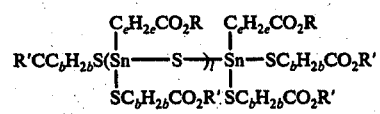

The preparation of alkoxycarbonylalkylenetin sulfide mercaptoalkylenecarboxylic acid esters according to this invention, as is evident from the above schemes I, II, and III proceeds in two steps starting from the alkoxycarbonylalkylenetin halides. It is not necessary, however, to separate or isolate the reaction product after each step. After the conversion of the alkoxycarbonylalkylenetin halide to the alkoxycarbonylalkylenetin mercapto alkylenecarboxylic acid ester halide, the alkali metal or alkaline earth metal sulfide can be added, while maintaining the pH below 10, and conversion to the sulfide then effected.

It is also possible to interchange the order of reaction steps in the preparation of alkoxycarbonylalkylenetin mercaptoalkylenecarboxylic acid ester sulfides. For example, the addition of sodium sulfide to a reaction mixture containing alkoxycarbonylalkylenetin halide and mercaptoalkylenecarboxylic acid ester can be carried out before, or simultaneously with, the addition of sodium hydroxide to the reaction mixture in whole or in part. Thus the reactants can be blended in any sequence, provided that the alkalinity is controlled at a pH below 10.

The reaction in each step proceeds in the presence of water, which serves as a solvent or vehicle for the alkali metal or alkaline earth metal hydroxide or sulfide, and the inorganic halide formed as a byproduct, as well as the alkoxycarbonylalkylenetin compound reactants and reaction products. The amount of water is not critical, but since the product must be separated therefrom at the conclusion of the reaction, there is no advantage in using more than is necessary to provide a fluid suspension or solution, that can be readily agitated for good mixing.

The reaction proceeds at room temperature, and is usually complete within less than one hour. However, reaction can be accelerated by use of an elevated temperature, preferably in the 35°–75° C range.

Any alkali or alkaline earth metal hydroxide, sulfide or polysulfide can be used in the preparation of alkoxycarbonylalkylenetin mercaptoalkylenecarboxylic acid ester sulfides, such as sodium hydroxide, potassium hydroxide, ammonium hydroxide, calcium hydroxide, barium hydroxide, or strontium hydroxide; sodium sulfide, lithium sulfide, potassium sulfide, calcium sulfude, barium sulfide, or strontium sulfide and the corresponding di- and poly-sulfides. Amine bases can also be used as acid acceptors, such as pyridine, triethylamine, tributylamine, triethanolamine, monoethanolamine, or diethanolamine.

The alkoxycarbonylalkylenetin mercaptoalkylenecarboxylic acid ester sulfides are soluble in water-immiscible organic solvents including paraffin hydrocarbons, and can be extracted therewith from the reaction mixture at the conclusion of the process. If they are insoluble in the reaction mixture, they can also be separated by filtration or centrifuging.

When alkoxycarbonylalkylenetin sulfides are available, as by way of the preparations according to this invention already outlined, these sulfides are also very convenient starting materials for conversion to alkoxycarbonylalkylenetin mercaptoalkylenecarboxylic acid ester sulfides according to this invention by reaction with an alkoxycarbonylalkylenetin mercaptoalkylenecarboxylic acid ester. This reaction takes place in high yield on warming together the reactants at 30°–90° C for time periods of 5 to about 500 minutes; even at room temperature and at temperatures as low as 5° C the same reaction takes place at a slower rate, requiring 2 to 3 days to reach completion.

The following equations illustrate the course of this reaction for different kinds of alkoxycarbonylalkylenetin sulfides and alkoxycarbonylalkylenetin mercaptoalkylenecarboxylic acid esters; R, R¹, L, b and e are defined as above.

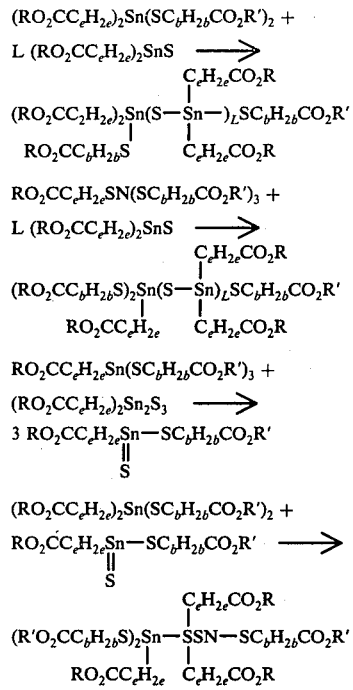

Alkoxycarbonylalkylenetin mercaptoalkylenecarboxylic acid esters that can be used include for example, 2-methoxycarbonylethylenetin tris(butylthioglycolate), 2-ethoxycarbonylethylenetin tris(isooctylmercaptopropionate), 2-butoxycarbonylethylenetin tris(stearylmercaptopropionate), 2-methoxycarbonyl-2-methylethylenetin tris(n-octylthioglycolate), 2-methoxycarbonylethylenetin tris(2-ethylhexylmercaptopropionate), bis(2-methoxycarbonylethylene)tin bis(isooctylthioglycolate), bis(2-methoxycarbonylethylene) tin bis(2-ethylhexylthioglycolate), bis(2-methoxycarbonylethylene) tin bis(2-ethylhexyl-3-mercaptopropionate), bis(2-butoxycarbonylethylene)tin bis(butylthioglycolate), bis(2-methoxycarbonylethylene)tin bis(stearylthioglycolate), bis(2-ethoxycarbonylpropylene) tin bis (laurylthioglycolate), bis(2-isopropoxycarbonylethylene)tin bis (isooctylthioglycolate) and bis(2-n-octyloxycarbonylethylene)tin bis isobutyl 3-mercaptopropionate.

The preparation of alkoxycarbonylalkylenetin sulfides according to this invention can be illustrated by the following examples.

EXAMPLE I

Bis(monoethoxycarbonylethylenetin)trisulfide

A dispersion of 65.2 g (0.2 mole) ethoxycarbonylethylenetin trichloride in 75 ml of water and 75 ml ethanol was warmed to 55° C. and a solution of 23.4 g (0.3 mole) sodium sulfide in 60 ml water was added from a dropping funnel with vigorous stirring. A warm water bath was used to keep the temperature of the reaction mixture between 60° and 75° C. The pH of the reaction mixture was measured periodically and the addition of the sodium sulfide solution was terminated when the pH had reached 6.2, at which time less than 1 ml remained in the dropping funnel. Stirring was continued for 2 hours at 60°–65° C and then while cooling to about 25° C. The product accumulated as a fine powder and was collected on a filter, washed with water and dried. The product had melting point 111°–121° C and infra-red absorption at 1680, 1720, and 1190 kaysers (in decreasing order of peak intensity), and analyzed 43.8% tin; $(C_2H_5OCOCH_2CH_2Sn)_2S_3$ requires 44.5% Sn.

EXAMPLE II

Bis(ethoxycarbonylethylene)tin sulfide

To a solution of 78.4g (0.2 mole) bis(ethoxycarbonylethylene)tin dichloride in 160 ml toluene was added 15.6g (0.2 mole) sodium sulfide as a 40% aqueous solution, while warming the mixture to maintain 85°–90° C. After the completion of the reaction, the layers were separated and the toluene solution of the product vacuum stripped to give the product as a viscous liquid, with refractive index 1.573 at 25° C and infra-red absorption peaks at 1700, 1660, and 1190. The product analyzed 33.9% tin, $(C_2H_5OCOCH_2CH_2)_2SnS$ requires 33.7% Sn.

EXAMPLE III

Bis(mono-n-octoxycarbonylethylenetin)trisulfide

The procedure of Example I was followed with the substitution of n-octoxycarbonylethylenetin trichloride as the starting material. A solid product was obtained with melting point 95°–103° C, infra-red absorption at 1680, 1720, and 1180, and 33.0% tin analysis; $(C_8H_{17}OCOCH_2CH_2Sn)_2S_3$ requires 33.9% Sn.

EXAMPLE IV

Bis(ethoxycarbonylethylene)tin 2-ethylhexyl thioglycolate sulfide

To 204 g (1 mole) 2-ethylhexylthioglycolate was added 392 g (1 mole) bis(ethoxycarbonylethylene)tin dichloride. The mixture was warmed to 40° C and 40 g (1 mole) sodium hydroxide as a 10% aqueous solution was added with stirring while keeping the temperature between 45° and 50° C, followed immediately by 39 g (0.5 mole) sodium sulfide as a 15% aqueous solution added until the pH was 6.7. The layers were separated and the heavy product layer vacuum dried to 85° C and filtered from a small amount of retained sodium chloride. The product was obtained as a fairly mobile liquid having refractive index 1.523 at 25° C and infra-red absorption at 1680, 1720, and 1190 kaysers. The product analyzed 21.8% tin; $S[(C_2H_5-OCOCH_2CH_2)_2SnSCH_2CO_2C_8H_{17}]_2$ requires 22.0% tin.

EXAMPLE V

Bis(ethoxycarbonylethylene)tin S,O-(2-carboxyethylene) sulfide

To a solution of 3-mercaptopropionic acid 21.2 g (0.2 mole) in 30 ml water at 40° C was added 78.4g (0.2 mole) bis(ethoxycarbonylethylene)tin dichloride with 60 ml 95% ethanol, followed by 21.8 g potassium hydroxide in 180 ml water. A gummy solid separated during the addition of the potassium hydroxide. The supernatant liquid was removed and the remaining solid washed with four 200 ml portions of warm (55°C) water and then allowed to air dry. There was obtained 72 g of pale tan solid.

EXAMPLE VI

Bis(methoxycarbonylethylene)tin S,O-(carboxymethylene)sulfide

PART A — Bis(methoxycarbonylethylenetin)dibromide 90.2 g (0.2 mole) was stirred into iso-octyl thioglycolate 81.6g (0.4 mole) at 60° C, followed by 16 g sodium hydroxide (0.4 mole) dissolved in 80 ml of warm water. The temperature during the addition was controlled at 60°–70° C. After the completed addition the mixture was stirred for 1 hour at 58°–63° C and the layers separated. The upper layer containing the bis(methoxycarbonylethylene)tin bis(isooctyl thioglycolate) was vacuum dried to 86° C and 20mm and filtered from a small quantity of solid. The filtrate was a pale yellow liquid with refractive index 1.508 at 25° C and tin analysis 16.42%; for $(CH_3OCOCH_2CH_2)_2$ Sn—$(SCH_2COOC_8H_{17})_2$ 17.0% Sn is calculated.

PART B — To 21 g (0.03 mole) of the above bis(methoxycarbonylethylene)tin bis(isooctyl thioglycolate)3g (about 10% excess thioglycolic acid was added dropwise. A white precipitate formed and was collected on a filter, and washed first with three portions of hexane and then with acetone, and dried. The resulting bis(methoxycarbonylethylene)tin S,O—carboxymethylene sulfide had melting point 190° to 200° C and analyzed 29.9% Sn. $(CH_3COCOH_2CH_2)_2Sn(SCH_2CO_2)$ requires 31.1% Sn.

1. EXAMPLE VII

Methoxycarbonylethylenetin(isooctyl thioglycolate) S,O–Carboxymethylene sulfide Methoxycarbonylethlenetin trichloride 98g (0.3 mole) was stirred into a mixture of isooctyl thioglycolate 61 g (0.3 mole) and thioglycolic acid 27.6g (0.3 mole) at 45° C. Sodium hydroxide solution (10% in water) was added dropwise with the temperature controlled at 45°–55° C, until a pH of 6.0 was reached; this required almost all of a 120g quantity of the solution. The layers were separated and the heavy product layer vacuum dried to 75° C. and filtered to give a pale yellow liquid product with refractive index 1.598 at 25° C.

EXAMPLE VIII

Ethoxycarbonylethylenetin(lauryl 3-mercaptopropionate) S,O-carboxyethlene sulfide Ethoxycarbonylethylenetin trichloride 65.3 g (0.2 mole) was stirred into a mixture of lauryl 3-mercaptopropionate 55g (0.2 mole) and 3-mercaptopropionic acid 21.2g (0.2 mole), and the mixture was reacted with sodium hydroxide and subsequently worked up as described in the preceeding example. The product was a slightly hazy liquid having refractive index at 25° C 1.519, and a tin content of 20.6%; the calculated tin content for $CH_3CH_2OCOCH_2CH_2Sn(SCH_2CH_2COO)SCH_2CH_2COOC_{12}H_{25}$ is 19.93%.

EXAMPLE IX

Bis(bis(methoxycarbonylethylene)tin(2-ethylhexyl thioglycolate) S,O-carboxyethylene sulfide 3-Mercaptopropionic acid 5.3g (0.05 mole) was added to bis(methoxycarbonylethylene) tin bis (2-ethylhexyl thioglycolate) 69.9g (0.1 mole). The reaction mixture became warm but remained homogeneous. The mixture was subjected to molecular distillation at 90° C and 0.005 mm to give 17.4g of distillate identified as 2-ethylhexyl thioglycolate; a control experiment without 3-mercaptopropionic acid gave upon molecular distillation only 0.8g of 2-ethylhexyl thioglycolate. The product was a light yellow viscous liquid that contained 20.7% tin; required for $(CH_3OCOCH_2CH_2)_2Sn\text{---}(SCH_2COOC_8H_{17})SCH_2CH_2COOSn\ (SCH_2COOC_8H_{17})\ (CH_2CH_2COOCH_3)_2$ 22.6% Sn.

Any rubber modified styrene polymer can be used with the alkoxycarbonylalkylenetin sulfides according to this invention. The rubber modified styrene polymers include physical blends of 3 to 50% by weight of rubbery 1,3-diolefin polymers, for example polybutadiene, polyisoprene, and SBR styrene-butadiene rubber in which butadiene constitutes at least 50% by weight of the monomers, with 50 to 97% by weight of styrene polymer resins, for example polystyrene, and styrene-acrylonitrile copolymers in which styrene constitutes at least 50% by weight of the monomers. Physical blends can be prepared by dry compounding, as by a rubber mill or Banbury mixer; or by mixing solutions of individual polymers and then removing solvent, or by blending and subsequently coagulating a latex of each polymer.

The rubber modified styrene polymers also include copolymers prepared by the simultaneous polymerization of styrene with a 1,3-diolefin and if desired, additional monomers whose presence as members of the polymer structure imparts desirable properties, for example acrylonitrile for outstanding solvent resistance and methyl methacrylate for transparency. Included among the copolymers are random copolymers, in which the arrangement of monomer units in the polymer structure is governed by the statistical probability of a given monomer unit entering the polymer structure in a given instant during its preparation, and various relatively ordered arrangements of the monomers in the polymer structure, such as block and graft copolymers.

Block copolymers are special cases of the so-called "living polymers" usually produced by anionic polymerization with alkali metal based initiators such butyl-lithium. These polymerizations usually are not subject to termination reactions, continue until the available monomer is exhausted, and can be restarted by fresh supply of monomer. When in such a polymerization a monomer, such as butadiene, is polymerized to exhaustion, i.e., a very small polymerization reaction rate resulting from low monomer concentration, a second monomer, such a styrene, can then be added and the polymerization continued with the result that the polymer structure produced has blocks consisting of a number of units only of the first monomer linked to a number of units consisting of the second monomer. Rubber modified styrene polymers that are block copolymers of styrene with a 1,3-diolefin, such as butadiene or isoprene, are characterized by having an elastomeric block of molecular weight 20,000 to about 1,000,000, preferably from 50,000 to 500,000, and a non-elastomeric polymer block which is a polymer of an alpha-olefin, preferably styrene, having an average molecular weight from 2000 to 115,000, preferably from 5000 to 50,000. Styrene-diolefin block copolymers can be hydrogenated to reduce the degree of unsaturation. A comprehensive disclosure of block copolymers by A. Hecker in U.S. Pat. No. 3,520,952 of July 21, 1970 is here incorporated by reference. Each of the block copolymers in this reference can be stabilized with a tin sulfide compound according to this invention.

When a monomer or monomer blend is polymerized in the presence of a polymer of another monomer, graft copolymers can be formed by chain transfer of a growing polymer chain with a preformed polymer, resulting at least in part in the growth of a branch chain or "graft" of one monomer on a "backbone" polymer of another monomer. From such a polymerization there usually results a mixture containing a graft copolymer of the monomers charged with the monomers present in the polymer initially present, together with a certain amount of polymer containing only units of the monomers charged. The presence of the graft copolymer promotes particularly intimate blending and compatibility of the various polymers present in admixture and results in products having particularly favorable impact strength properties.

Graft copolymers can contain as little as 3% to as much as 50% polymerized 1,3-diolefin and from 50 to 97% polymerized styrene or combination of styrene and third monomer. The third monomer if present can be acrylonitrile, methyl methacrylate, methacrylonitrile, and alphamethylstyrene; proportions of styrene to third monomer are such that there is at least 50% by weight of styrene based on the combined weight of styrene and third monomer.

Graft copolymers are usually prepared by emulsion polymerization, i.e., styrene and third monomer when used are polymerized in the presence of a latex of butadiene or butadiene copolymer. An explanation of this process by C. Bawn at Column 2 lines 3 to 36 of U.S. Pat. No. 3,352.820 is here incorporated by reference.

Graft copolymers of a 1,3-diolefin with styrene or styrene and a third monomer can also be prepared by a solution polymerization method in which the "backbone" polymer and monomers are dissolved in a common solvent from which the graft polymer precipitates as it is formed. The solution method is particularly suited to stereospecific rubbery polymers such as high cis-polybutadiene which are not readily obtained in an aqueous latex form. A description of a solvent process for preparing rubber-modified styrene-acrylonitrile copolymers as well as the graft polymers obtained by the process by H. Weitzel at Column 2 line 5 to Column 4 line 21 of U.S. Pat. No. 3,449,471 is here incorporated by reference.

Alkoxycarbonylalkylenetin sulfides according to this invention are readily compounded into rubber-modified styrene polymers. Conventional dry mixing procedures, such as cold mixing with powder or granular polymer, and hot mixing by a rubber mill or Banbury mixer are suitable. Alkoxycarbonylalkylenetin sulfides are also well suited to blending into a rubber modified styrene polymer latex before the usual coagulating and drying steps in working up the polymer. The alkoxycarbonylalkylene sulfides are unaffected by passing through this procedure and help protect the polymer against harmful effects of heat exposure during drying as well as subsequent processing and use. Only small amounts of alkoxycarbonylalkylene sulfide are required, such as 0.005 to 5% by weight of the polymer being stabilized.

Rubber modified styrene polymers containing alkoxycarbonylalkylenetin sulfides according to this invention are processed by any of the conventional fabricating methods such as injection molding, extrusion, calendering, thermoforming, and blow molding. Products such as pipe, pipe fittings, refrigerator and freezer parts, luggage, telephone sets, bottles and golf club heads can be fabricated. A discussion of fabricating techniques and uses by H. Keskkula in "Encyclopedia of Polymer Science and Technology", 13 (1970) pages 415-425 is here incorporated by reference.

Alkoxycarbonylalkylenetin sulfides exert a favorable influence on the flow properties of rubber modified styrene polymers at process temperatures and are useful in enabling high output rates of extruders and screw injection molding machines to be achieved. Further improvements in production rates as measured, for example, by the length of flow in a spiral mold at a given temperature as well as lessened tendency to attract electrostatic charge can be achieved by using in combination with the alkoxycarbonylalkylene tin sulfide at least one amide or group II metal salt of a monocarboxylic acid having 6 to 26 carbon atoms, preferably in a ratio of 0.2 to 5 parts by weight of amide or salt for each part by weight of alkoxycarbonylalkylenetin sulfide.

Useful amides include, for example, linoleamide, behenamide, N,N'-ethylene bis(stearamide), bis(hydroxyethyl)tetradecanoamide, and 1,6-di(hexadecanoamido)hexane. Group II metal salts that can be used include for example, magnesium benzoate, strontium laurate, calcium palmitate, barium myristate, and zinc p-t-butylbenzoate. A comprehensive disclosure of Group II metal salts that can be used by M. Minagawa in U.S. Pat. No. 3,849,370 Column 22, line 66 to column 23 line 35 is here incorporated by reference.

Additional stabilizers that can be used in rubber modified styrene polymers according to this invention include phenolic antioxidants such as BHT, thiodipropionate esters such as dimethyl, dilauryl, ditridecyl and distearyl thiodipropionates, and epoxidized esters, such as epoxy soybean oil, epoxylinseed oil, and isodecyl epoxystearate. Comprehensive disclosures of phenolic, and thiodipropionate stabilizers in U.S. Pat. No. 3,849,370 column 16 line 49 to column 22 line 65, and epoxide ester stabilizers by M. Minagawa in U.S. Pat. No. 3,869,324 column 26 lines 12 to 39 are here incorporated by reference.

Stabilizer compositions of alkoxycarbonylalkylenetin sulfide and amide or Group II metal salt in accordance with this invention can be in solid, liquid or paste form. Liquid compositions can be prepared by blending the ingredients and heating at 40° to 140° C for up to 6 hours to achieve visual homogeneity and storage stability. Inert ingredients that can be added to the stabilizer compositions to improve their handling convenience include solvents such as hydrocarbons, 2-ethylhexanol, isodecyl alcohol, 2-ethoxyethanol, and 2(2-butoxyethoxy)ethanol; paste consistency modifiers such as finely divided silica, polyethylene glycols and polypropylene glycols and their monoalkyl and monoaryl ethers, and water; anticaking agents such as talc, magnesium trisilicate, sodium silicoaluminate, and aluminum calcium silicate. The following are nonlimiting examples of liquid stabilizer compositions that can be prepared in accordance with this invention:

| No. | Ingredients | Grams | Heated at ° C | Hours |
|---|---|---|---|---|
| I | Bis(2-ethoxycarbonylethylenetin) sulfide | 40 | 50° | 1 |
|  | Barium 2-ethylhexoate | 10 | | |
|  | 2-ethoxyethanol | 25 | | |
|  | Aromatic naphtha b.p. 160-190° C | 18 | | |
| II | Epoxysoybean Oil | 20 | 80° | 1 |
|  | Calcium neodecanoate | 25 | | |
|  | 2-methoxycarbonylethylenetin(isooctylthioglycolate)-3-mercaptopropionate | 55 | | |
| III | Bis (hydroxyethyl) | 15 | 60° | 2 |
|  | Calcium 2-ethylhexoate | 20 | | |
|  | 2-methoxycarbonylethylenetin(isooctylthioglycolate)-bis (2-methoxycarbonylethylene)tin isooctylthioglycolate sulfide | 65 | | |

The following are non-limiting examples of solid stabilizer compositions that can be prepared in accordance with this invention:

| No. | Ingredients | Grams |
|---|---|---|
| IV | Barium stearate | 47 |
|  | Bis (2-methoxycarbonylethylene)tin 3-mercaptopropionate | 49 |
|  | BHT antioxidant | 4 |
| V | Calcium stearate | 44 |
|  | Bis (2-methoxycarbonylethylene)tin sulfide | 34 |
|  | Bis (2-methoxycarbonylethylene) tin sesquisulfide | 22 |
| VI | N,N'-ethylene bis(stearamide) | 21 |
|  | Strontium stearate | 12 |
|  | Bis (2-ethoxycarbonylethylenetin)sesquisulfide | 62 |

The following are non-limiting examples of paste stabilizers compositions that can be prepared in accordance with this invention:

| No. | Ingredients | Grams |
|---|---|---|
| VII | Epoxylinseed Oil | 65 |
|  | Bis (2-butoxycarbonyloxyethylenetin) isooctylthioglycolate sulfide | 15 |
|  | Magnesium palmitate | 20 |
| VIII | Epoxysoybean oil | 70 |
|  | BHT antioxidant | 5 |
|  | Calcium stearate | 10 |
|  | Bis (2-methoxycarbonylethylenetin) 3-mercaptopropionate | 15 |

The following examples, in the opinion of the inventors, represent the preferred practice of their invention.

EXAMPLES 1 to 3

In order to demonstrate the improved viscosity stability and color stability upon heating of ABS resin polymer compositions according to this invention, compositions of the following formulation were tested and results obtained shown in Table 1.

To determine viscosity stability, the change in melt viscosity was measured at 200° C by a Plasticorder torque recording mixer. (Measuring condition: air atmosphere, mixer capacity 50cc, rotor speed 60 rpm).

To determine heat stability, pellets were prepared by extrusion of powdered premix at 200° C, injection molded into 3.5 × 2.5 × 0.1 cm plaques at 230° C, and aged by heating for 10 to 20 hours in a Geer aircirculating oven at 135° C. The reflectance by Hunter colorimeter was measured and the percent whiteness compared.

(FORMULATION)

| Unstabilized ABS resin | 100 parts |
|---|---|
| Additives (Table I) | 1.0 |

TABLE I

| No. Control | Additives | Amount | Variation Of Melt Viscosity | | | Heat Color Before Heating | Stability 135° C × 10 hrs. | Whiteness % 135° C × 120 hrs. |
|---|---|---|---|---|---|---|---|---|
| | | | Torque after 10 min. | Torque after 120 min. | Difference of the Torque | | | |
| A | Dibutyltin bis (isooctylthioglycolate) | 1.0 | 1.98 | 2.17 | 0.19 | 49.3 | 25.4 | 20.6 |
| B | Dibutyltin mercaptopropionate polymer | 1.0 | 1.97 | 2.20 | 0.23 | 49.2 | 24.6 | 20.4 |
| C | Dimethyltin bis (isooctylthioglycolate) Dimethyltin sulfide polymer | 0.8 0.2 | 1.99 | 2.15 | 0.16 | A49.8 | 25.0 | 20.9 |
| D | NONE | — | 2.00 | 2.20 | 0.18 | 47.3 | 24.4 | 18.6 |
| 1 | Bis [bis(2-methoxycarbonylethylene) tin isooctylthioglycolate]sulfide | 1.0 | 1.97 | 2.00 | 0.03 | 52.5 | 46.0 | 38.6 |
| 2 | Bis (2-ethoxycarbonylethylene) tin mercaptopropionate polymer | 1.0 | 1.95 | 1.98 | 0.03 | 53.4 | 43.8 | 34.9 |
| 3 | 2-butoxycarbonylethylenetin tris (butylmercaptopropionate) bis (2-butoxycarbonylethylene) tin sulfide polymer | 0.8 0.2 | 1.97 | 1.99 | 0.02 | 50.8 | 40.4 | 32.6 |

The results of the viscosity stability and oven aging tests show that acrylonitrile-butadiene-styrene polymer containing a new tin sulfide compound of this invention is remarkably constant in viscosity even after two hours of masticating and in color stability far superior to the polymer not containing the new tin sulfide compound of this invention.

EXAMPLES 4 to 6

In order to examine the color protection of rubber modified polystyrene resin composition of the invention, performance test was carried out using the rubber modified polystyrene resin polymerized according to the following formulation.

| Synthetic rubber (Butadiene 75 parts, styrene 25 parts) | 7.5 parts |
|---|---|
| Styrene Monomer | 92.5 |
| Potassium Persulfate | 0.1 |
| Disproportionated rosin sodium soap | 1.0 |
| n-Dodecylmercaptan 0.05 | |
| Water | 200 |

Polymerization was carried out as follows:

Water, initiator and emulsifying agent were charged in a reaction vessel and mixed completely, then synthetic rubber was added and styrene monomer. Polymerization was carried out at 70° C for 10 hrs., and the polymer was obtained by salting-out with calcium chloride, followed by dehydrating with centrifugal separator, washing with water and drying at 80° C for 5 hours.

The rubber modified polystyrene resin obtained in this manner was ground then passed through an extruder at 200° C and pelletized according to the following formulation, injection molded the pellets at 230° C, and aged by heating in Geer oven at 135° C for 20 hours. The reflectance by Hunter colorimeter was measured and compared with the whiteness.

(FORMULATION)

| Rubber modified polystyrene resin | 100 parts |
|---|---|
| Additives (Table 2) | 0.1 |

TABLE 2

| No. | ADDITIVES | WHITENESS % |
|---|---|---|
| Control | | |
| E | 2,6-di-t-butyl-p-cresol | 17 |
| F | Trisnonylphenylphosphite | 16 |
| G | Dimethyltin bis (isooctylthioglycolate) | 22 |
| H | NONE | 15 |
| 4 | 2-ethoxycarbonylethyltin mercaptopropionate polymer | 34 |
| 5 | bis [2-methoxycarbonylethyltin bis (isooctylmercaptopropionate] disulfide | 32 |
| 6 | bis (2-methoxycarbonylethyl)tin sulfide polymer | 30 |

The results of the oven aging shown that color stability of rubber modified styrene polymer containing the new tin sulfide compounds of this invention is far superior to such polymer containing conventional additives.

We claim:

1. A sulfide compound of four-valent tin having linked to tin through carbon from 1 to 2 alkoxycarbonylalkylene groups having 1 to 8 carbon atoms in the alkoxy group and 2 to 3 carbon atoms in the alkylene group, and directly linked to tin at least one bivalent sulfide group, represented by one of the formulae

and

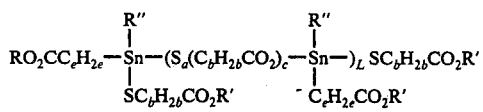

in which R is an alkyl group having from 1 to 8 carbon atoms, R' is a hydrocarbon group having from 4 to 18 carbon atoms, R" is $-C_eH_{2e}CO_2R$ or $-SC_bH_{2b}CO_2R'$ $a$ is an integer from 1 to 4, $b$ is 1 or 2, $c$ is 0 or 1, $d$ is 1 or 2, $e$ is 2 or 3, $n$ is from 1 to about 100 and L is a number from 1 to 10, provided that when $d$ is 2, $a$ is at least 3.

2. A tin sulfide compound according to claim 1 in which each bivalent sulfide group consists of one sulfur atom.

3. A tin sulfide compound according to claim 1 having at least one sulfide group consisting of a plurality of sulfur atoms.

4. A tin sulfide according to claim 1 having at least one sulfide group which is a carboxyalkylene sulfide with 1 to 2 carbon atoms in the alkylene group.

5. A tin sulfide compound according to claim 1 having the formula $$[S_a(C_bH_{2b}CO_2)_cSn_d(C_eH_{2e}CO_2R)_2]_n$$

in which R is an alkyl group having from 1 to 8 carbon atoms, $a$ is an integer from 1 to 4, $b$ is 1 or 2, $c$ is 0 or 1, $d$ is 1 or 2, $e$ is 2 or 3, and $n$ is from 1 to about 100, provided that when $d$ is 2 $a$ is at least 3.

6. A tin sulfide compound according to claim 1 having the formula

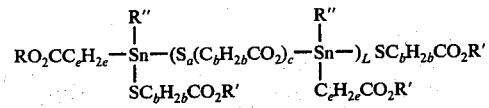

in which R is an alkyl group having from 1 to 8 carbon atoms, R' is a hydrocarbon group having 4 to 18 carbon atoms, R'' is $-C_eH_{2e}CO2R$ or $-SC_bH_{2b}CO_2R'$, $a$ is an integer from 1 to 4, $b$ is 1 or 2, $c$ is 0 or 1, $e$ is 2 or 3, and L is a number from 1 to 10.

7. A tin sulfide compound according to claim 5 in which $a$ is 3 and $d$ is 2.

8. A tin sulfide compound according to claim 5 in which $a$ is 1 and $c$ is 0.

9. A tin sulfide compound according to claim 5 in which $a$ is 1, $c$ is 1, and $d$ is 1.

10. A tin sulfide compound according to claim 6 in which $c$ is 0.

11. A tin sulfide compound according to claim 7 which is 2-ethoxycarbonylethylene-tin sulfide.

12. A tin sulfide compound according to claim 7 which is 2-n-octoxycarbonylethylene-tin sulfide.

13. A tin sulfide compound according to claim 8 which is bis(2-ethoxycarbonylethylene)-tin sulfide.

14. A tin sulfide compound according to claim 9 which is bis(2-ethoxycarbonylethylene)tin S,0-(2-carboxyethylene)sulfide.

15. A tin sulfide compound according to claim 10 which is bis(2-ethoxycarbonylethylene)tin 2-ethylhexyl thioglycolate sulfide.

16. A rubber-modified styrene polymer composition comprising polymerized styrene and polymerized aliphatic 1,3-diolefin and 0.005% to 5% by weight of the polymer composition of a tin sulfide compound according to claim 1.

17. A rubber-modified styrene polymer composition according to claim 16 comprising polymerized styrene and polymerized 1,3-butadiene.

18. A rubber-modified styrene polymer composition according to claim 16 comprising styrene, 1,3-butadiene, and acrylonitrile.

19. A rubber-modified styrene polymer composition according to claim 16 comprising styrene, 1,3-butadiene and methyl methacrylate.

20. A rubber modified styrene polymer composition according to claim 16 comprising a block copolymer of styrene and 1,3-butadiene having a non-elastomeric polymer block of styrene units with an average molecular weight within the range from 20,000 to 120,000 and an elastomeric polymer block of 1,3-butadiene units with an average molecular weight within the range from 20,000 to 1,000,000.

21. A composition able to improve the processability and color of a rubber modified styrene polymer upon heating comprising an amide or Group II metal salt of a carboxylic acid having 8 to 26 carbon atoms and a tin sulfide compound according to claim 1.

22. A composition according to claim 21 in which the amide is ethylenebisstearamide.

23. A composition according to claim 21 in which the Group II metal salt is calcium stearate.

24. A composition according to claim 21 in which the Group II metal salt is barium stearate.

* * * * *